(12) United States Patent
Dignam et al.

(10) Patent No.: US 9,295,575 B1
(45) Date of Patent: *Mar. 29, 2016

(54) BRAIDED ORTHOTIC PRODUCTS AND METHODS OF MANUFACTURE

(71) Applicant: Mentis Sciences, Inc., Manchester, NH (US)

(72) Inventors: John J. Dignam, Methuen, MA (US); Patrick P. McDermott, Vienna, VA (US); Christopher S. Anderson, Epson, NH (US)

(73) Assignee: Mentis Sciences, Inc., Manchester, NH (US)

( * ) Notice: Subject to any disclaimer, the term of this patent is extended or adjusted under 35 U.S.C. 154(b) by 34 days.

This patent is subject to a terminal disclaimer.

(21) Appl. No.: 14/018,161

(22) Filed: Sep. 4, 2013

Related U.S. Application Data

(60) Provisional application No. 61/696,433, filed on Sep. 4, 2012.

(51) Int. Cl.
*B29C 70/42* (2006.01)
*A61F 5/01* (2006.01)

(52) U.S. Cl.
CPC .................... *A61F 5/0102* (2013.01)

(58) Field of Classification Search
CPC ............... A61F 5/0102; A61F 5/0109; A61F 2005/0132; A61F 2005/0134; A61F 2005/0155; A61F 5/0123; A61F 5/0125; A61F 5/0127

USPC ............ 156/148, 149; 623/33, 32, 34, 35, 36, 623/37, 38; 87/8, 9

See application file for complete search history.

(56) References Cited

U.S. PATENT DOCUMENTS

| | | | | |
|---|---|---|---|---|
| 6,024,005 A | * | 2/2000 | Uozumi | ............................ 87/34 |
| 8,690,962 B2 | * | 4/2014 | Dignam et al. | ................. 623/33 |
| 2008/0234836 A1 | * | 9/2008 | Taylor | ................... A61F 2/5046 623/33 |
| 2012/0179272 A1 | * | 7/2012 | Dignam et al. | ................. 623/33 |

* cited by examiner

*Primary Examiner* — Jacob T Minskey
*Assistant Examiner* — Vishal I Patel
(74) *Attorney, Agent, or Firm* — James Creighton Wray; Meera P. Narasimhan

(57) ABSTRACT

This invention provides new above knee (AK) and below the knee (BK) orthotic devices and implements specific manufacturing processes for the production of orthotic devices through the automated, computer controlled bi-axial and tri-axial braiding of orthotic devices, over a mold or mandrel made of carved foam, plaster material or wax that is a replica of the patient's limb, and is created by a Computer Aided Design (CAD) file controlling a Numerically Controlled (CNC) machine tool. This method of manufacture using aerospace fibers such as graphite or Kevlar, and high performance resins, is used to create a orthotic device which is stronger and lighter weight than conventionally manufactured orthotic devices. Braiding also allows incorporation of woven cloth, tapes and other reinforcements into the braiding process for added strength at selected areas. The method dramatically decreases the production time and cost of the relative to conventional methods.

10 Claims, 12 Drawing Sheets

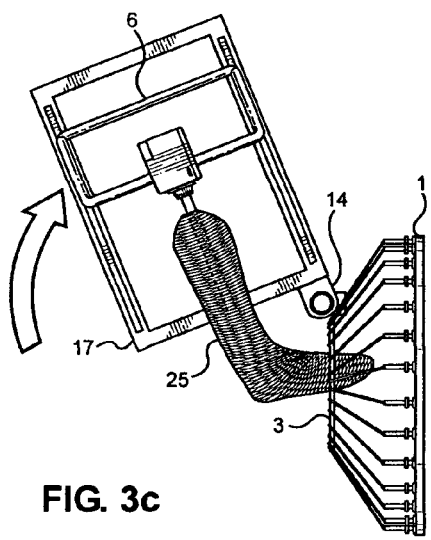
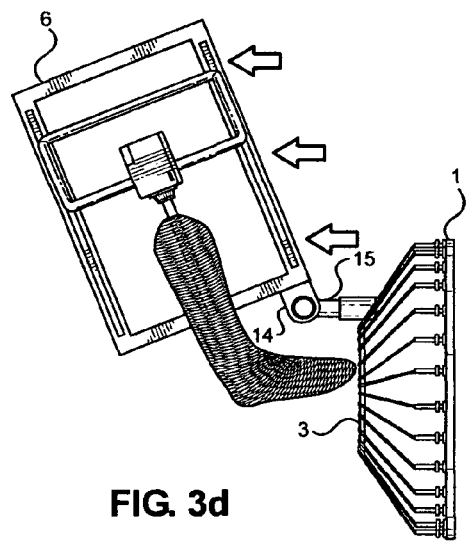
FIG. 3c
FIG. 3d

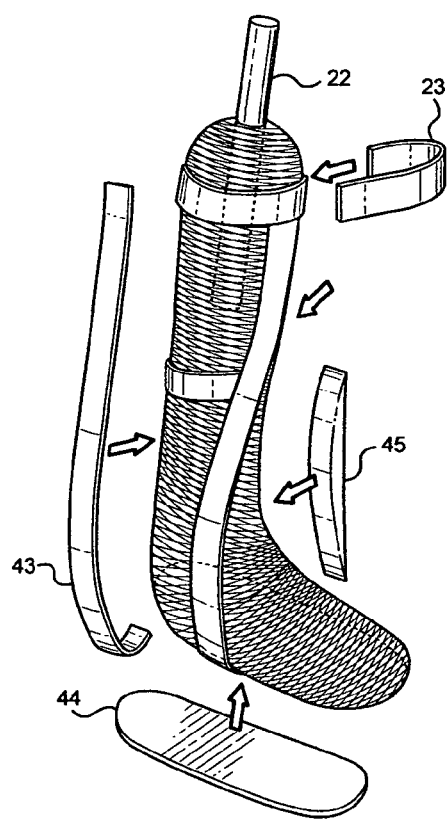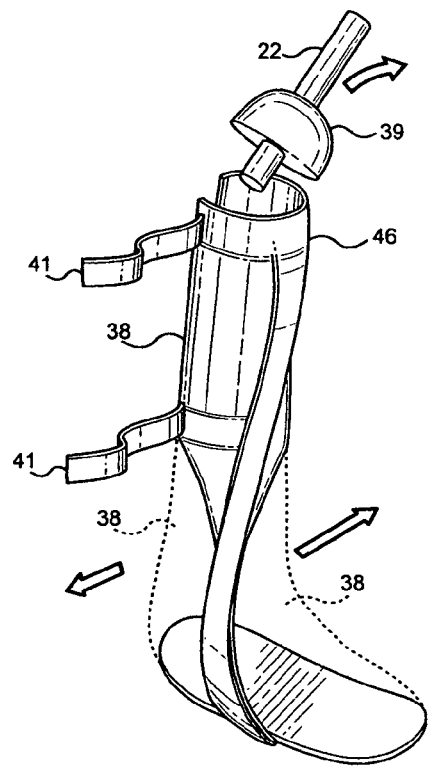
FIG. 6a  FIG. 6b

BRAIDED ORTHOTIC PRODUCTS AND METHODS OF MANUFACTURE

BACKGROUND OF THE INVENTION

1. Field of the Invention

The present invention relates to processes related to the manufacture of orthotic products using textile braiding techniques, with aerospace quality fibers, resins, and inserts to produce lighter weight, stronger, lower cost, and better fitting orthotic products on standard braiding equipment modified with attachment of special support structures to aid manufacture.

2. Description of the Prior Art

An orthesis is a device that is used to support, align or correct deformities or weaknesses in the spine, arms or legs, and to improve the function of the movable parts of the body. An Ankle Foot Orthosis (AFO) is an orthotic device for the lower limb that encloses the ankle and foot and does not extend above the knee. The Knee Ankle Foot Orthosis (KAFO) is an orthotic device for the lower limb that extends from above the knee to the ankle and foot. To correct spinal deformations, the Lumbosacral Orthosis (LSO) is a spinal orthosis that encircles the body in the lumbosacral region. There are also orthopedic devices for the upper limbs including arm, forearm, wrist, hand and thumb, as well as braces for stabilizing the neck and head.

In general, the orthopedic brace or appliance is used to: 1) control, guide, limit or immobilize and extremity, joint, or body segment; 2) restrict movement in a certain direction, or assist movement where appropriate: 3) reduce weight bearing forces on weakened joints: 4) aid rehabilitation from fractures, when casts are removed; 5) correct the shape of function of a part of the body to provide easier movement or reduce pain.

Orthopedic appliances come in all shapes and sizes and depending on the severity of the injury or deformation. Some can be purchased "as is" and strapped on the limb as a temporary brace or splint. But these generally cannot be used for correcting serious deformities or injuries which may require a "custom" fit, so that the supporting orthotic member or element conforms to the curvature of the body or limb to give maximum support.

Some orthotic devices like back braces can be made to conform to the person's anatomy, for example, the lower portion of the back by heating a relatively thick piece of thermoplastic material until pliable, then pressing into the lower lumbar region of the patient while the material is flexible. After cooling, the plastic is rigid, and can be inserted into a cloth covering that contains Velcro straps or belts to position the device against the back and supports it.

This type of "customizing" will not work for other situations, however, like spinal correction, where the orthopedic device is not simply to replicate the current condition, but rather to create a different alignment by moderate pressure on the torso by means of a customized orthotic device that creates the realignment.

The invention described below is a method of producing orthotic devices through textile braiding that are form fitting to the patients limbs and torso, but are made with high strength materials that are lighter in weight than the thick plastic materials described above and generally stronger. Like other custom orthotic products, braided products require that a solid model of the bodily part to be generated representative of the shape of that part, whether it is portions of an arm or leg, or, in the case of a spinal correction, the whole torso of the individual.

Traditionally, production of custom fit orthotic products starts with the creation of a cast of the patient's limb or torso using plaster of Paris wraps or bandages to map the shape of the bodily part. After the wrap has hardened, it is carefully removed and is used as a mold for the casting of a positive plaster mold, a replica of the body part, with a pipe embedded in the mold to facilitate handling. After the mold has set, the plaster wrap or bandage is removed.

The plaster mold or cast can be modified by the orthotics technician, known as a orthotist, by adding or subtracting material based on the orthotist's knowledge and experience of the body and its distinctive characteristics. This process of modification is referred to as rectification. The orthotist uses the cast rectification to produce a better distribution of interface pressures between the orthotic device and the limb during usage.

Alternatively, instead of casting a positive plaster replica of the limb in the hardened plaster wrap or bandage taken from the patient, some fabrication facilities create a digitized solid model computer file by scanning the inside of the patient's plaster wrap with a mechanical sensor or laser scanner. This digitized image can then be modified by computer software designed for this purpose to dimensionally add or subtract "material" from the digitized image in a manner similar to that of the technician adding or shaving material off the plaster cast to adjust or fine tune the cast to better replicate the body part.

Alternatively, a computer generated solid model can be derived from data taken directly from the surface of the limb or torso by means of various imaging devices that scan the surface of the skin and create a computerized image of the patients limb or torso. This is the preferred method of generating a computer image, hereafter referred to as the computer Solid Model, or Computer Aided Design (CAD) file of the bodily part. There is software available that can modify this CAD file electronically to "rectify" the shape as described above, adding or subtracting material digitally for a better fit, for example, by adding thickness to the model for padding or liners between the orthotic structure and the skin of the patient.

Once the CAD file is generated, it can then be loaded into computer controlled CNC machine tool often referred to as a "carver", which cuts out a replica of the body part, plus enhancements for padding and liners, in a rigid but malleable material like a high density polymeric foam or a machine able wax. At this point, a thermoforming material can be drawn over the positive mold making a negative replica of the body part.

The next step in the conventional production process of a custom fit orthotic is to secure fabrics (graphite cloth or fiberglass weave) to the mold adding additional layers as needed depending on the required strength of the orthotic device prior to introduction of a resin matrix material to stabilize the structure of the part.

Typically, the next part of the process involves a Vacuum Assisted Resin Transfer Mold (VARTM) process where a vacuum bag is secured around the exterior of the mold containing the fiber/cloth layup and resin is introduced under a vacuum, and then manually "massaged" around the assembly to assure the cloth laminate is fully wetted. After the resin is cured, the mold is removed through scrapping out the foam, chipping out plaster, or liquefying the wax.

Some of the conventional processes suffers from a number of drawbacks. One, the wrap-casting process is somewhat messy and labor intensive as are many of the subsequent steps in the formation of orthotic product. Secondly, if the orthetist does not make a digitized solid model of the limb, there is not a permanent record of either the initial plaster wrap representing the shape of the limb, or the subsequent negative plaster mold, or, more importantly, the rectified plaster mold, since it has to be broken out the mold to complete the production of the appliance. Since there is no record of the shape of the limb or torso, the whole process has to be repeated if the orthotic product is damaged, does not fit properly or needs minor adjustments later because of weight gain or loss. The need exists for improved methods and structures for making orthotic appliances.

The invention described below is aimed at lowering the cost of conventional methods for producing custom orthotic products in a wide variety of forms and applications using textile braiding, which is rapid, repeatable, light weight, utilizing molds and mandrels based on computer-generated solid models of the patient's limbs and torso. The invention relates to the methods of manufacture where additional fixtures are added to the standard braiding machine to accommodate complex shapes like a full leg and ankle orthotic product where a standard braider/gantry machine cannot easily maneuver the mold through the braider assembly.

SUMMARY OF THE INVENTION

This invention provides enhancements to the standard braiding machine in order to produce a variety of orthotic device geometries for arms, legs, and complete body shape. The enhancements implements specific manufacturing processes for the production of orthotic devices through the automated, computer controlled bi-axial and tri-axial braiding of orthotic devices, over a mold or mandrel made of carved foam, plaster or thermoset material in the conventional manner, created by a Computer Aided Design (CAD) file on a Numerically Controlled (CNC) machine tool. The CAD file is created from at 3-D digital image of the patient's limb generated by a laser scanner or other sensing mechanism.

The method of manufacture allows some flexibility in the use of low cost fibers and weaves, like hemp or glass fiber, for areas of the orthotic where strength and stiffness are moderate. High strength aerospace fibers, tapes and cloth such as graphite or Kevlar, are used to strengthen areas of higher stress.

The objective is to create an orthotic device which is stronger and lighter weight than conventionally manufactured orthotic devices, and generates a very accurate negative replica of the patient's limb, thus adding to the comfort of the patient. Braiding also allows incorporation of woven cloth and reinforcements into the braiding process for added strength at selected areas, for example, where cut outs may be desired or appliances like hinges or fastening straps are added to the base orthotic device structure.

The method is capable of dramatically decreasing the production time and cost of the orthotic relative to conventional methods, which are very labor intensive. The CAD file can be retained for future use in the generation of additional orthotic devices which may be needed to replace lost or broken orthotic devices. Or, the process can be repeated for serial production of orthotic products. The orthotic devices produced in this manner by the textile braiding process are stronger and lighter weight. The lighter weight especially benefits the patient, since weight of the orthotic product is often linked to other secondary effects like hip problems induced by heavy limbs.

The automation of the braiding process as described in this invention allows the operator to "engineer" the orthotic device during the production process, by varying the lay down of fiber or fiber tow on the mandrel by adjusting the speed of the gantry and braider to open up and/or close the braid, thus adjusting the angle between the fibers or tows. This affects the fiber density which is also adjustable, depending on the strength requirements of the orthotic device. By regulating the tension on the fibers, the operator is also able to achieve a more compact weave of fibers. This has an additional beneficial effect, from a cost and weight point of view, of requiring less resin.

The "engineered" orthotic device with reinforcements at locations of stress at can be fabricated in most cases with two to three layers of braided fiber, with reinforcements interleaved between the braided fiber layers. Using these reinforcements, with low cost fiber for the bulk of the structure can reduce overall cost of the orthotic product.

Accordingly, it is a principal object of the invention to apply automated composite manufacturing processes (braiding) to the production of an improved orthotic products using 3-D digital images of the limb to produce mandrels that are replicas of the limb or torso of the patient.

It is another object of the invention to use the flexibility of the braiding process to reduce the amount of fiber or fiber tow, as well as resin, to produce an "engineered" orthotic device that is lighter weight and lower cost than conventionally produced orthotic devices.

It is also an object of the invention to incorporate woven cloth or strips and cutouts of cloth made from high performance fibers, between the layers of braided material to strengthen and reinforce areas of the orthotic device where cutouts are required or hard points established for addition of hardware, straps or other products to complete the integration of the orthotic.

It is another object of the invention to integrate a braider manufacturing cell where the operator can adjust the gantry and braider speeds, as well as tension on the fiber or fiber tow so that the composite requires less fiber and resin while maintaining the necessary orthotic device strength for the patient.

It is another object of the invention to reduce manufacturing costs through reduced direct labor and materials costs, including recycling and reuse of materials like recovery of wax mandrel material which can be melted and reused.

It is another object of the invention to improve durability and strength of the orthotic device and attachment hardware, which allows for the production of lighter weight orthotic devices.

It is another object of the invention to closely match the contours of the limb or torso which adds to the comfort of the patient.

It is another object of the invention to retain a 3-D digital image of the orthotic device to facilitate modification of the orthotic device for improved fit, and/or remanufacture a orthotic device if lost or damaged.

It is another object of the invention to accomplish the whole manufacturing process in a much shorter time than conventional processes, thus further reducing cost and inconvenience to the patient.

The overall s manufacturing process can be summarized as follows: 1) The patient's needs are identified including height, weight, and specific purpose of the orthotic device; 2) A 3-D model of the limb is created using various sensing techniques, such as laser scanners; 3) Molds are created using computer controlled machine tools; 4) The 3-D model can modified to allow for foam liners, hardware attachment points or other special requirements; 5) The mold is used as a mandrel in a bi-axial or tri-axial braiding machine which forms varied layers of fibers, impregnated with resin; 6) The resin is cured; 7) Hardware is attached to complete the orthotic product.

These and further and other objects and features of the invention are apparent in the disclosure, which includes the above and ongoing written specification, with the claims and the drawings.

BRIEF DESCRIPTION OF THE DRAWINGS

Various features and attendant advantages of the present invention will become more fully appreciated when considered in conjunction with accompanying drawings, wherein:

FIGS. 3a, 3b, 3c, and 3d show top views of the mandrel support structure attached to the leg mandrel in FIG. 1a (3a), the leg mandrel being transported linearly through the braider up to the ankle (3b), the support structure rotating through an angle for braiding of the ankle area (3c), and finally the linear motion of the support structure to for braiding of the foot (3d).

FIGS. 6a and 6b, shows perspective views of an Ankle Foot Orthosis (AFO) similar to that designed by Allard with graphite strip reinforcements added to the FIG. 1a mandrel (6a), with mandrel material and cutouts removed for installation of fastening hardware (6b).

DETAILED DESCRIPTION OF THE PREFERRED EMBODIMENTS

Figure 1A:
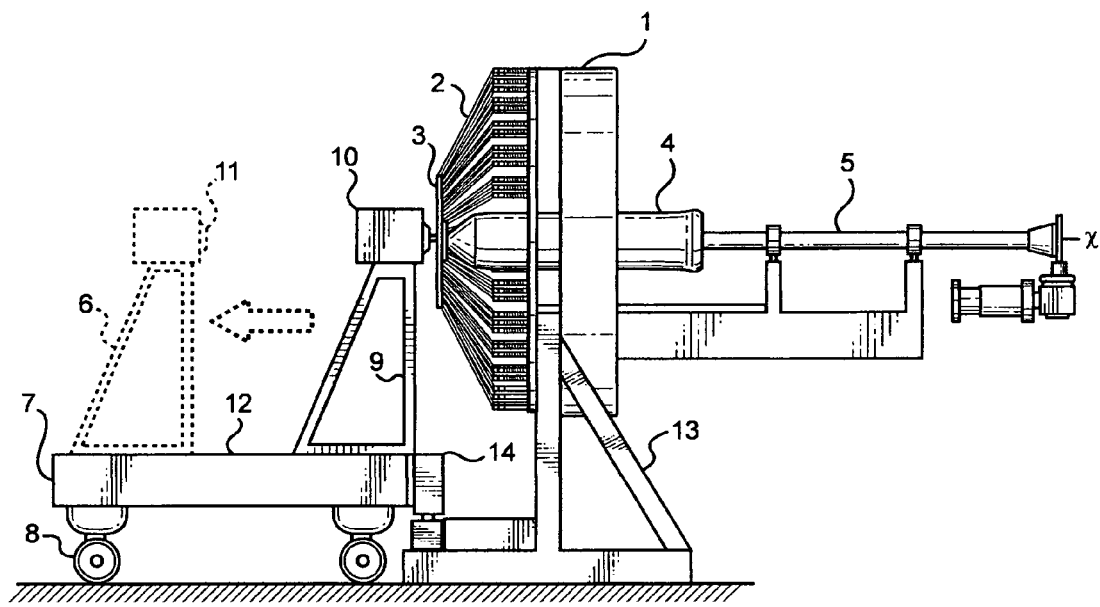
FIGS. 1a 1b, 1c, 1d, 1e, 1f, and 1g show various views of a braider manufacturing cell with braider, gantry, and a rotatable mandrel support structure (1a), the end view of the support structure (1b), a top view of the support structure rotated about a post (1c), a top view of the support structure translated by the linear motion of the post (1d), side view of a simplified mandrel support structure (1e), an end view of the simplified support structure (1f), the top view of the simplified support structure (1g).

FIG. 1a, shows a conventional braiding manufacturing cell with the addition of a specialized support structure on the left hand to aid in the braiding of unusually shaped objects as might be encountered in development of the orthotic products. The braider cell consists of a braider head 1 which lays down fiber 2 via a braider head ring 3 onto a mandrel 4 which is positioned by and centered by a linear carrier system 5, hereafter referred to as the gantry. The gantry is able to transport the mandrel back and forth along axis x through the center of the ring 3 as the fiber is laid down on the mandrel.

The mandrel support structure 6 on the left consists of a cart like base 7 supported on casters 8 which in turn supports a slideable receiving frame 9 with receiving head 10 able to grasp the mandrel with clamps 11. This frame is able to move support structure 6 on tracks 12 from right to left with gantry 5 providing the linear motion through ring 3. During manufacture, the gantry feeds the mold assembly back and forth through the braider as the various layers of fiber 2 are laid on the mandrel 4. The gantry can be controlled via a desk top computer through an electronic infrastructure, for example, Contrex, M-Trim controllers connected to the computer through RS-422 communication ports. The support structure 6 is attached to the base of the braider 13 by means of a rotatable joint 14 attaching support base 7 to the braider base 13.

Figure 1B:
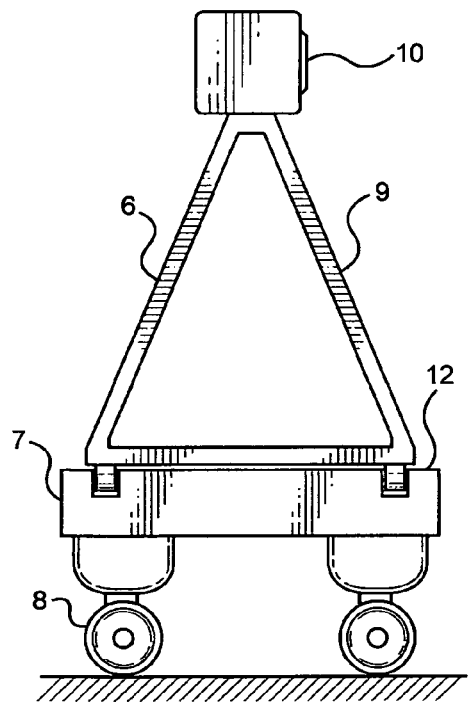

FIG. 1b is and end view of the mandrel support structure 6 with base 7 supporting the receiver structure 9 and head 10 which can move back and forth along embedded track 12.

Figures 1C, 1D:
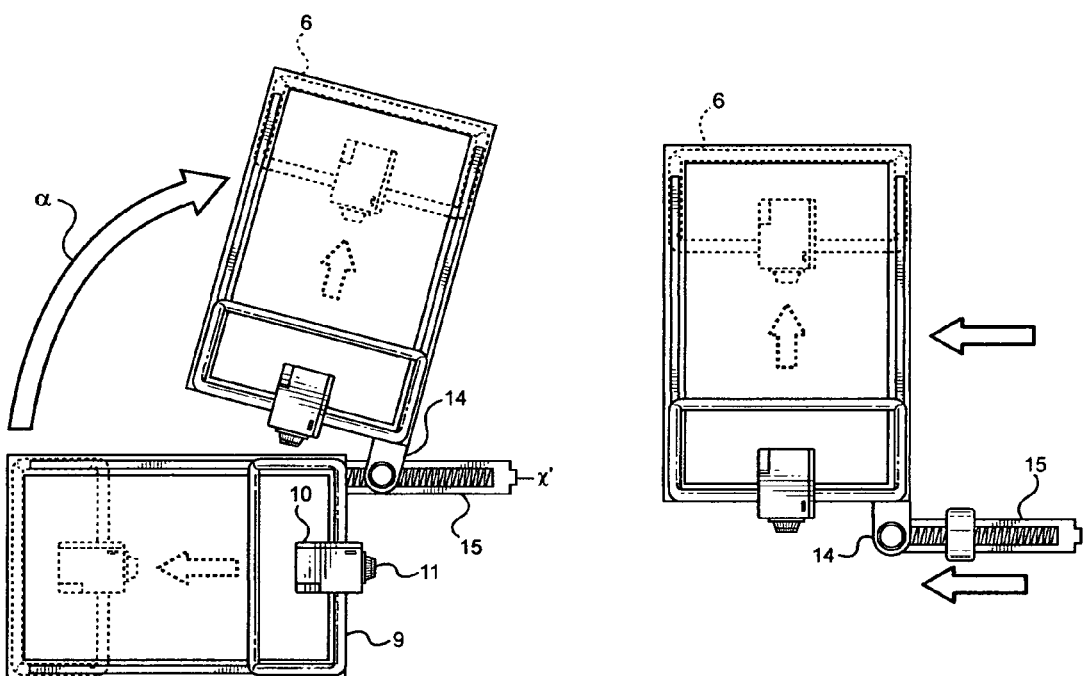

FIG. 1c is a top view of the support structure 6 being rotated through angle α about joint 14 which itself is able to be transported along the axis x' by a smaller and shorter stroke gantry system parallel to axis x of the main gantry.

FIG. 1d shows a top view of support structure 6 being translated to the left by gantry 15 via rotatable joint 14. The casters 8 on support base 7 allow the whole support structure 6 to be rotated about joint 14 as well as being translated in the x' direction by gantry 15. All of these linear and rotational motions are required to braid a complex shape.

The speed of the gantry 5 feeding the mandrel 4 and the speed of braider 1 laying down fiber 2 is controlled by a computer with software which automatically adjusts the speeds of each in order to achieve the optimal angle and density of fibers laid down. The operator is also able to control the process via a manual controller.

Mentis Sciences Computer Automated Braiding System (MSCABS) developed by Mentis Sciences Incorporated, MSI, is used to fabricate accurate, and repeatable, state of the art textile structures. This is accomplished by collecting feedback data such as braid speed and gantry position, and using this to calculate and continuously control the braider and gantry speeds and create the desired laminate composite structure.

The control speeds are determined by the geometry of the part being fabricated (specified by CAD model) and with user input providing braid angles that are determined by patient requirements. By controlling braid angle as a function of axial location and ply number, the system can tailor the mechanical properties of the structure being fabricated to the needs of a patient's requirements. This technology thus enables efficient manufacturing of complex, patient-specific orthotic devices.

Figure 1E:
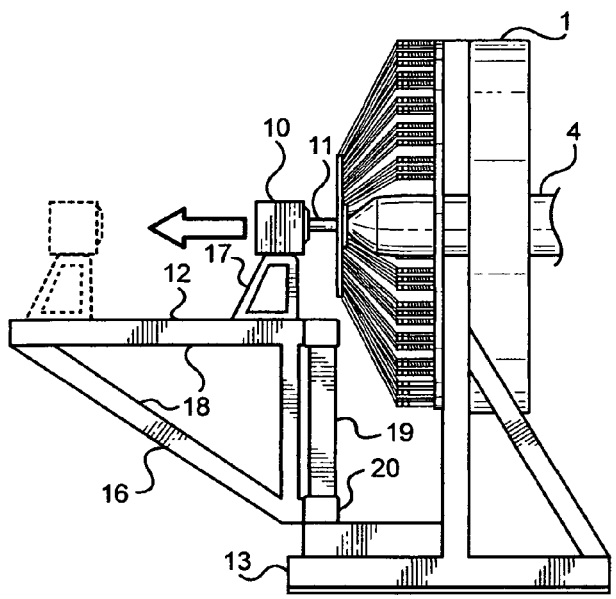
Figure 1F:
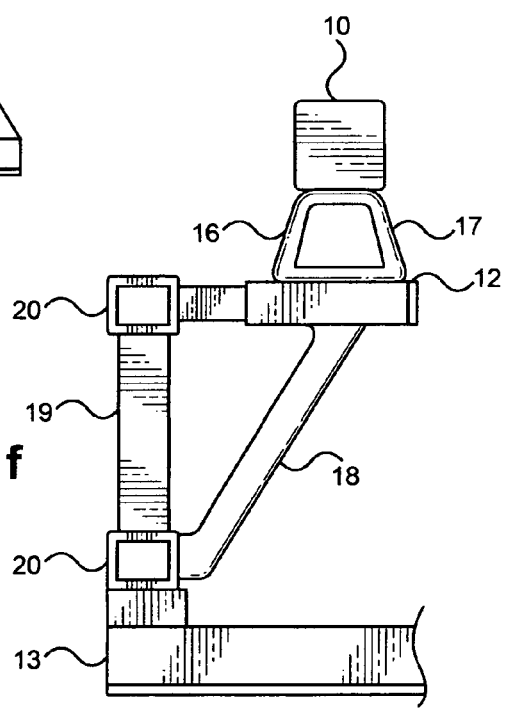
Figure 1G:
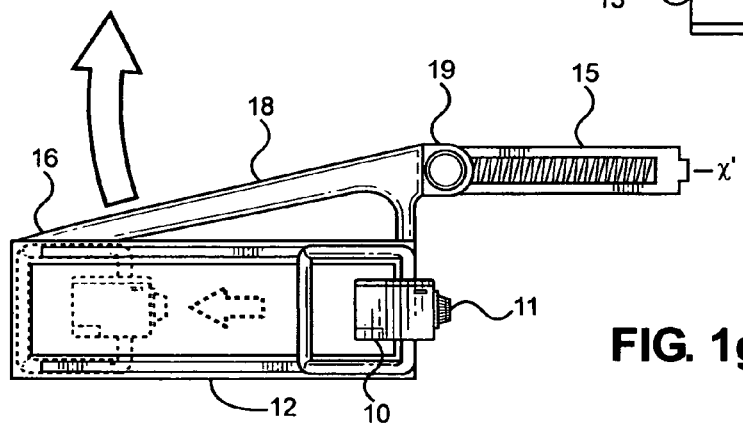

FIGS. 1e, 1f, and 1g show views of a simplified mandrel support structure 16. FIG. (1e) is a side view, where head 10 mounted on frame 17 attached to mandrel 4 via clamps 11, is able to support mandrel 4 as frame 17 as it translated from right to left on tracks 12. The tracks are supported in turn by a frame 18 attached to a post 19 through rotatable joints 20.

FIG. (1f) is an end view of 16 with post 19 firmly attached to braider base 13, with upper and lower rotatable joints 20 stabilizing frame 18 and allowing it to rotate around post 19.

FIG. (1g) is a top view of 16, with frame 18 rotating clockwise around post 19. Post 19 is anchored to the braider base structure and is driven in the x' direction by gantry 15, with motion similar to the motion shown in FIG. 1d.

Figure 2A:
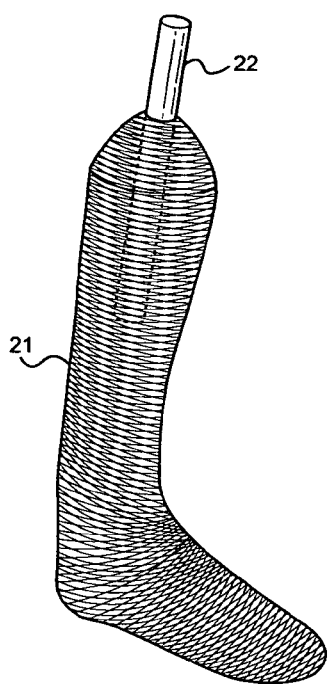
FIGS. 2a, and 2b show of a perspective view of a full-up leg mandrel with and initial layer of braid (2a) and the braided mandrel with reinforcing materials adhered to the mandrel in strategic locations (2b).
Figure 2B:
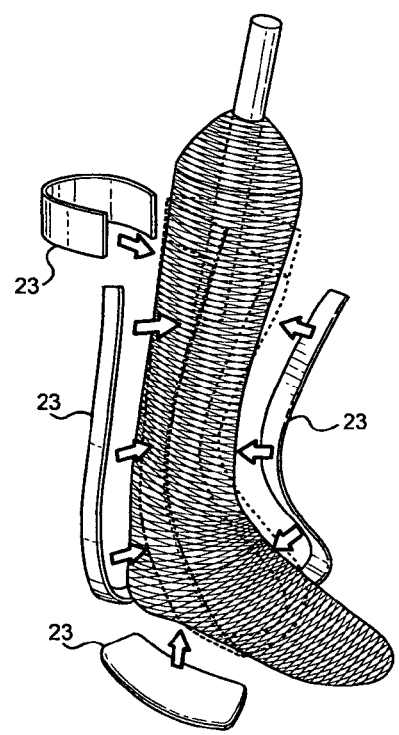

FIGS. 2a, and 2b show of a perspective view of a full-up leg mandrel 21 with and initial layer of braid (2a) and the braided mandrel with reinforcing materials 23 adhered to the mandrel in strategic locations (2b) prior to the next layer of braid.

FIGS. 3a, 3b, 3c, and 3d show top views of the mandrel support structure 6 during the braiding of a complex mandrel like that shown in FIG. 2a, with the movements required to achieve the braiding of a complex shape.

Figure 3A:
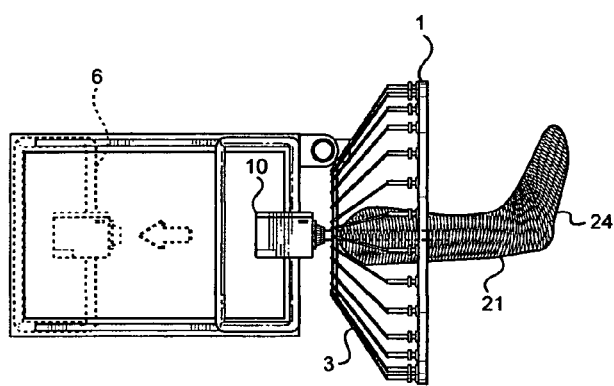

FIG. 3a shows a top view of the support structure 6 set up prior to the lay down of additional braid layers after placement of the reinforcement strips 23. The support structure is attached to pipe 22 embedded in leg mandrel 21 via clamp 11 on receiver head 10. Additionally, the base of the leg mandrel can be attached to gantry 5 by means of a clamp at location 24 to facilitate controlled motion through braider head ring 3.

Figure 3B:
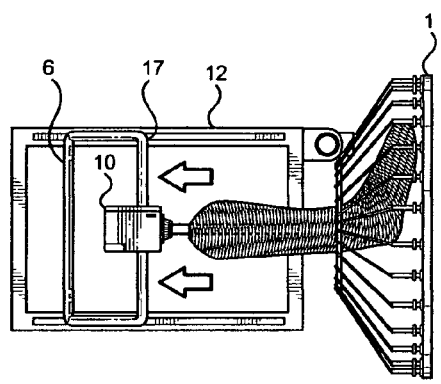

FIG. 3b shows an additional layer of braid being applied to mandrel 21 as it moves from left to right with the aid of gantry 5, being supported by receiving head 10 and frame 9 that moves linearly along tracks 12.

In FIG. 3c, the base of the mandrel is removed from gantry 5 at location 24 to allow the mandrel to be rotated around joint 14 for the lay down of additional braid in the ankle area. To stabilize the mandrel near the braider ring 3, an additional fixture could be used to clamp the mandrel to the support base 7 at location 25.

FIG. 3d shows the final braiding step where the rotational joint 14 is locked down, allowing gantry 15 to provide a linear translational motion for the braiding of the foot area through the braider head ring 3. Once all of the braiding is accomplished, the fibers are separated from the braider head by cutting through the fibers in the toe area of the mandrel. The next step is the application and curing of resin to provide the stiffness of the final part.

Figure 4A:
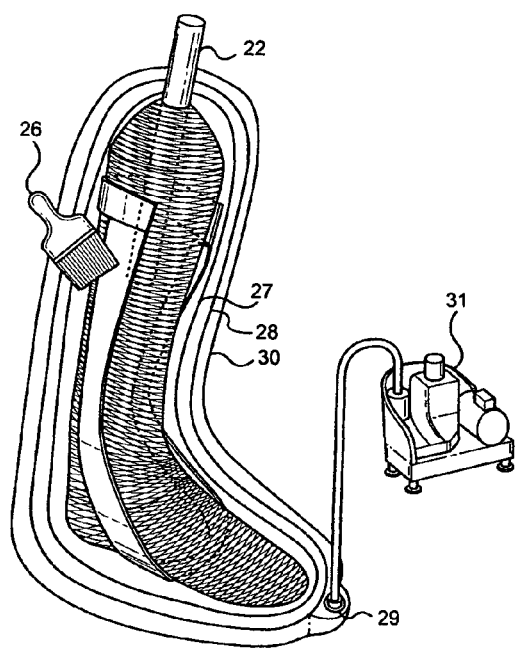
FIGS. 4a and 4b show two ways of applying resin to the braided material by brushing it onto specific areas that will be cured for the final product (4a), and a Vacuum Assisted Resin Transfer Mold (VARTM) process where a vacuum bag is secured around the exterior of the mold for consolidation and curing of the part (4b).
Figure 4B:
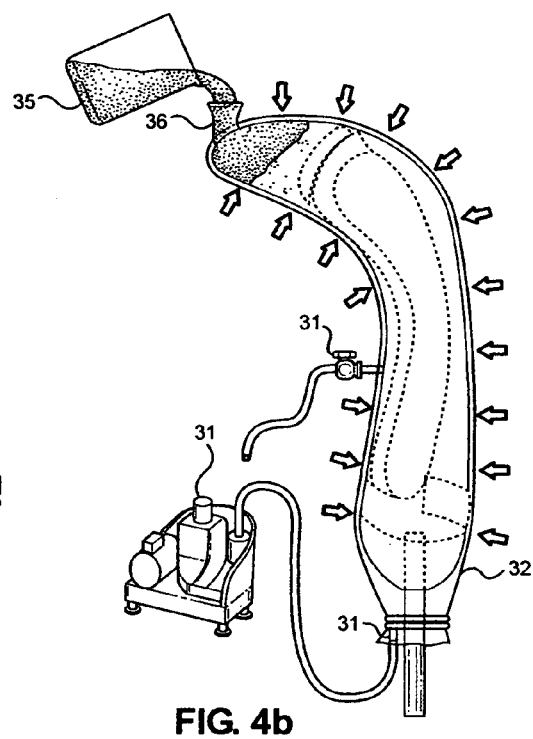

FIGS. 4a and 4b show two ways of applying resin to the braided material by brushing it onto specific areas that will be cured for the final product (4a), and a Vacuum Assisted Resin Transfer Mold (VARTM) process where a vacuum bag is secured around the exterior of the mold for consolidation and curing of the part (4b).

FIG. 4a shows resin being applied manually with a brush 26, which is only one of several means of applying the resin. Once the first layer is laid down on the mandrel, resin can be sprayed, rolled or brushed on manually, or applied manually with a spatula and smoothed out over the layers of the fiber material. The important point here is that amount of resin applied can be carefully controlled by the operator to avoid waste and assure even distribution of resin. No resin need be applied to areas which will ultimately be removed as cut outs.

After resin has been applied by whatever method, a consolidation process is required to assure the resin is distributed evenly throughout the laminate which includes braided material as well as reinforcement strips and cloth. In this process, layers of material are required for vacuum bagging and consolidation with the first layer being a peel ply 27, then with a breather cloth 28, with a vacuum fitting 29 on the breather cloth and an outer layer 30 serving as the vacuum bag. These loose wrappings are taped over the mold, with a vacuum applied by vacuum pump 31 which compresses and de-bulks the cloth and braided materials prior to curing.

The assembly is then is cured at an appropriate temperature. Curing factors may include temperature, pressure, vacuum and time. The required temperature and pressure is dependent by the resin type (thermo-plastic, or thermo-set). After curing the wrappings 27, 28, and 30 are removed.

FIG. 4b shows the alternative VARTM method of resin infusion and curing, a method used extensively in the prosthetics manufacturing business. Here the mandrel is locked into a base via the pipe 22 and with a polyvinyl PVA bag pulled over the braided mandrel and secured to a base fixture 33 that incorporates an attachment point 34 for pulling a vacuum by means of pump 31. Resin 35 is then poured into an opening 36 at the top of the PVA bag, and "messaged" down the braided mandrel under vacuum, to assure total wetting of the braided and cloth insert material. Excess resin collects in the bottom and is discarded. A secondary connection 37 to the vacuum pump is shown which could augment the resin flow in larger or longer orthotic products. The secondary valve would be closed when the resin front reaches the vicinity of connection 37.

Figure 5A:
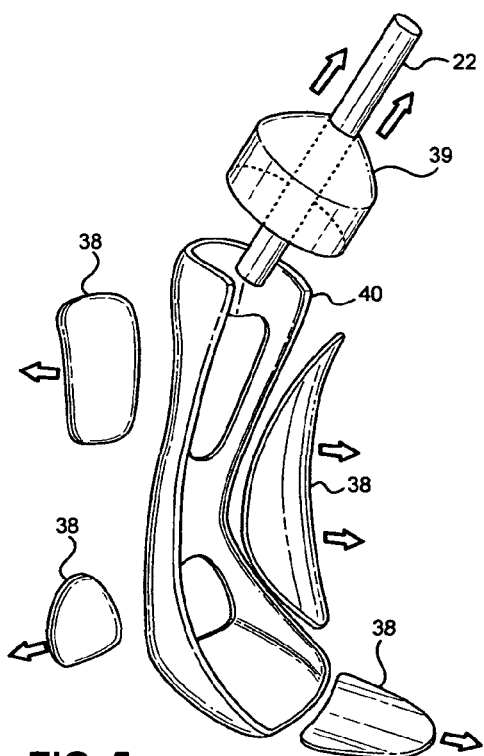
FIGS. 5a and 5b show perspective views of the cured part where mandrel material and cut outs are removed (5a), and hardware is inserted to complete the product (5b).
Figure 5B:
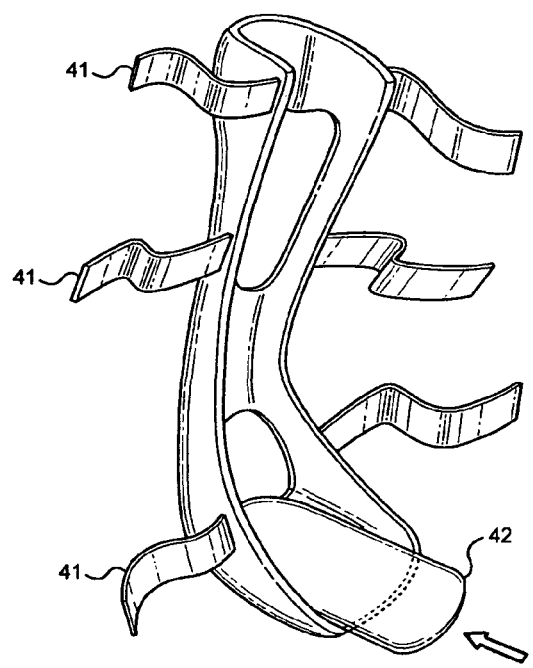

FIGS. 5a and 5b show perspective views of the cured part where mandrel material and cut outs are removed (5a), and hardware is inserted to complete the product (5b).

In FIG. 5a, much of the material in the braided mandrel representing a Knee Ankle Foot Orthosis (KAFO) is removed by cutting out exterior pieces 38 of the post cured hard shell, and removing the cap 39 with its embedded pipe 22. As the exterior shell segments are removed, the original mandrel material can be more easily removed to expose the basic structure 40 of the KAFO.

FIG. 5b shows the final integration of the KAFO with the addition of straps and fasteners 41 and a foot conforming insole 42.

FIGS. 6a and 6b, shows perspective views of an Ankle Foot Orthosis (AFO) similar to that designed by the Allard company with graphite strip reinforcements added to the FIG. 1a mandrel (6a), with mandrel material and cutouts removed for installation of fastening hardware (6b). This approach could be used with any orthotic of similar style where stiff or spring like graphite epoxy structures are used to connect one major part with another.

FIG. 6a shows a different layup of reinforcements than shown in previous figures, with as multilayered graphite strip 43 which attached to a conforming multilayered insole 44, provides the primary support structure for this KAFO. The primary supporting member 43 is curved outward around the ankle area from the basic leg mandrel 21 and can be formed in one of two ways: 1) by adding a conformal wedge 45 to mandrel 21 before the layup of fiber, or 2) the addition of the wedge digitally to the original CAD file, which will then be carved into the foam or other mandrel material prior to fiber layup and curing.

FIG. 6b shows the extensive removal of exterior shell segments around the ankle area, the whole back section, and the top 39 with its embedded pipe 22 to produce a form fitting structure 46, open at the back with fastener straps 41 added to secure the orthotic to the leg.

Figure 7A:
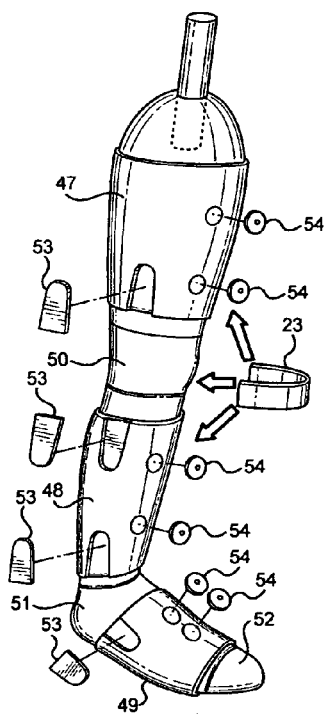
FIGS. 7a, 7b, and 7c show perspective views of multiple orthotic products braided onto a mandrel representing a leg, with inserts (7a), hardware and fasteners being affixed to the devices after removal from the mandrel (7b), and multiple orthotic products braided onto a mandrel representing a patient's arm (7c).
Figure 7B:
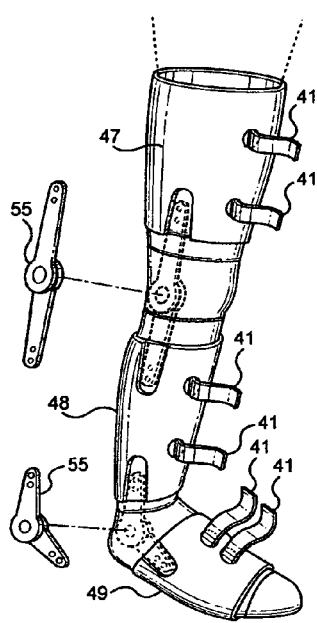
Figure 7C:
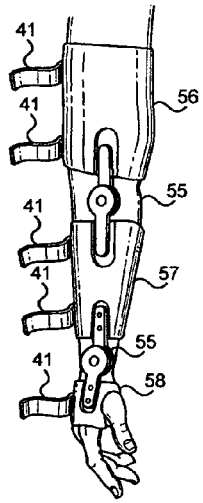

FIGS. 7a, 7b, and 7c show perspective views of multiple orthotic products braided onto a single mandrel like that shown in FIG. 1a with reinforcement inserts at strategic locations (7a), hardware and fasteners affixed to the orthotic devices after removal from the mandrel (7b), and multiple orthotic products braided onto a mandrel representing a patient's arm (7c).

FIG. 7a show development of three separate orthotic products 47, 48 and 49 which represent three different devices, the uppermost enclosing the thigh, 47, the middle enclosing the calf, 48, and the lower enclosing the foot, 49, with, in the process of manufacture, the majority of fiber and inserts is concentrated in these areas, with very little material laid down by the braider in the area of the knee 50, the ankle 51, or the toe 52. In order to lay minimal fiber in these open areas, the gantry is speeded up with the controls described above so that little material is laid down and wasted in the areas which will essentially be cut away when the three upper, middle and lower products are separated out front the mandrel.

Two or three of these composite laminate structures will be utilized, after curing, in forming AFOs or KAFOs with metal hinges connecting the upper to the middle and middle to lower in the KAFO and middle with lower only for the AFO. It is important, therefore, that reinforcements be strategically placed during the braiding process to provide stout foundations for the metal hinges that will carry much of the weight of the patient.

In FIG. 7a, there are three types of reinforcements that will be adhered to the braided product during manufacture: 1) graphite, Kevlar, or other strips 52 placed at the cut lines on the top and bottom of each of the three objects, and in cut lines where the orthotic has to be "opened up" to fit around the limb; 2) graphite, Kevlar, or other patches 53 strategically locations where hinging hardware is to be placed and anchored; 3) patches where straps 41 with fasteners will be anchored to close the orthotic around the limb. All of the reinforcements are added to the braided mandrel before the braiding of the last and final layer of braid.

FIG. 7b shows the incorporation of hardware and straps to the upper, middle and lower composite laminate structures 47, 48, and 49 with the metal hinges affixed to the reinforced pads 53 incorporated into the laminate, and straps and fasteners 41 appropriately located to close the orthotic on the limb.

FIG. 7c shows the incorporation of hardware and straps to the three composite laminate structures 56, 57, and 58 that correspond to the upper arm, forearm, and hand, with metal hinges affixed to the reinforced pads incorporated into the laminate, and straps and fasteners 41 appropriately located to close the orthotic on the limb.

FIGS. 8a, 8b, 8c and 8d shows variation of full body torso orthotics with a frontal view of high strength reinforcing material strips and patches applied at appropriate locations (8a), a side view of the same (8b), and a perspective view of the orthotic removed from the mandrel with straps and fasteners applied for securing the orthotic to the patient (8c), and addition of an upper leg orthotic for hip support (8d). Full body torso orthotics 59 come in many shapes and sizes, with cut outs similar to those illustrated in other figures, anterior, posterior, or lateral cut lines 60 where hinges or pliable materials allow the orthotic to be opened up then closed on the body and secured with straps and fasteners 42, or Velcro strips to secure the molded parts onto the body.

Figure 8A:
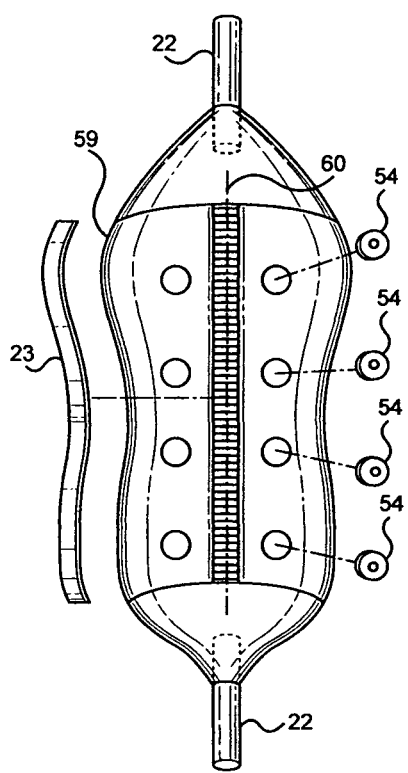
FIGS. 8a, 8b, 8c and 8d show full body torso orthotics with a frontal view of high strength reinforcing material strips and patches applied at appropriate locations (8a), a side view of the same (8b), a perspective view of the orthotic removed from the mandrel with straps and fasteners applied for securing the orthotic to the patient (8c), and, finally, a side view of the torso orthotic linked via hinge to a leg orthotic for support of the hip (8d).

FIG. 8a is a frontal view of an orthotic with anterior cut line 60 for opening and closing or could be a posterior view with a hinging material at the cut line to add flexibility for donning the orthotic device. The torso has pipes 22 embedded in both the top and the bottom of the mandrel for potentially securing and stabilizing it at both ends, in the fixtures attached to gantry 5 to the rear of the braider head, and in the front, to support structure 6 via clamp 11 in the receiver head 10. This would allow for stout control of a large torso mandrel as it passes through the braider head ring 3.

Figure 8B:
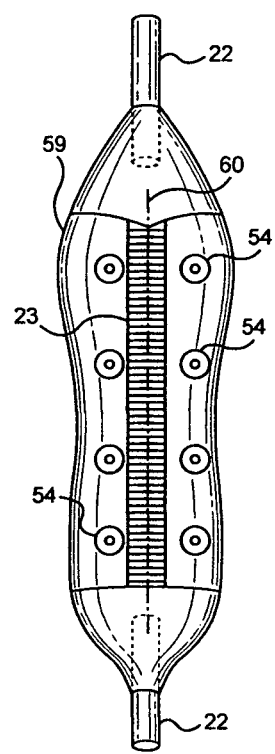

FIG. 8b is a side view of orthotic 59 with a lateral cut line 60 reinforced with strips 23 and patches 54 for attaching fasteners.

Figure 8C:
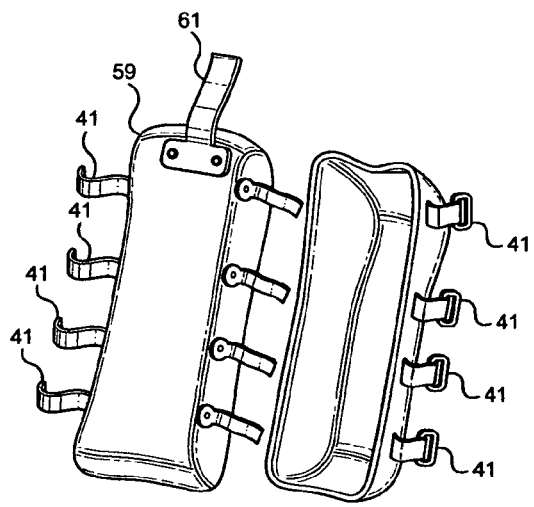

FIG. 8c is a perspective view of orthotic 59 with straps and fasteners 41 attached with optional addition of fixture 61 to support neck and head braces.

Figure 8D:
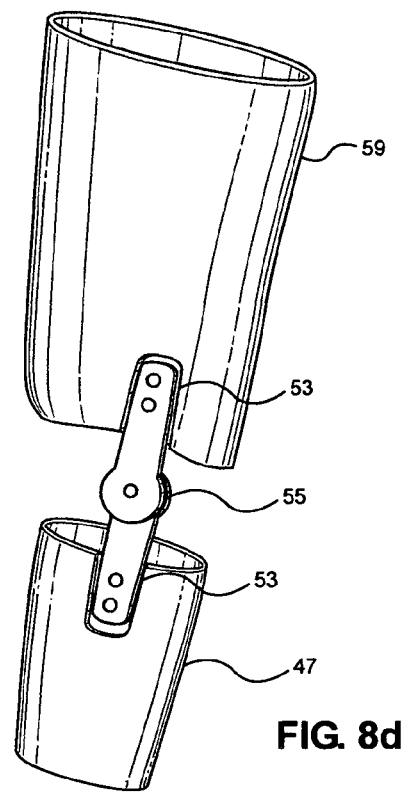

FIG. 8d shows a common configuration for support of the hip where the torso orthotic 59 is linked to an upper leg orthotic 47 via a binge 55 which is attached to hard points on each part, reinforced with high strength cloth patches 53 braided into each part.

We claim:

1. A method comprising:
   producing a limb orthotic device consisting of unitary or multiple composite sleeves with straps to compress the limb orthotic device on a residual limb, with rotatable joints and hinges connecting multiple composite sleeves constructed by utilizing textile braiding techniques,
   producing limb measurements,
   forming a limb shape from the measurements,
   forming a plastic film or thermoset layer over the limb shape,
   braiding the limb orthotic device and forming a braided orthotic device, and
   removing the limb shape from an interior of the braided orthotic device.

2. The method of claim 1, further comprising impregnating the braided orthotic device with resin and curing and hardening the resin.

3. The method of claim 2, wherein the impregnating comprises:
   placing a sleeve around the braided orthotic device, reducing pressure within the sleeve introducing the resin at one end of the sleeve around the braided orthotic device, forcing the resin along the braided orthotic device in the sleeve, curing the resin, and removing the sleeve.

4. The method of claim 2, wherein the impregnating comprises: brushing, spraying, or manually laying resin on the braided layers, placing a sleeve around the braided orthotic device, and
   reducing pressure within the sleeve until the resin is cured.

5. The method of claim 1, further comprising:
   braiding the fibrous tows back and forth over the limb shape to form braided layers of fibrous material, placing woven cloth strips or cutouts on previously braided layers of woven material, and securing the cloth strips in place with additional layers of braided material, providing hard points for connection of straps and hinges by incorporating treaded metal strips or plates between braided layers for securing straps and hinges by means of bolts, screws or other fasteners.

6. The method of claim 1 further comprising mounting the limb shape and thermoset layer on a gantry or multiple gantries feeding the limb shape into a braider and wherein the braiding comprises braiding a first biaxial or triaxial layer on the thermoset layer, and braiding a second biaxial or triaxial layer on the first biaxial or triaxial layer, and so on until sufficient layers of braided material are achieved.

7. The method of claim 6 wherein cloth reinforcements and threaded metal strips or plates are added between biaxial or triaxial layers to strengthen the orthotic product in areas that encounter mechanical stress such as anchoring points for adding hardware such as hinges, and straps for securing the orthotic product to the patient.

8. The method of claim 1 further comprising mounting the limb shape on a gantry feeding the first end of the limb shape into a braider and with the second end of the limb shape held by a screw driven secondary gantry on a cart or rotatable structure bearing the secondary gantry as a mechanism for retracting the limb shape at the opposite end of the braider plane.

9. The method of claim 7 further comprising a screw driven secondary gantry on a cart or rotatable structure bearing the secondary gantry as a method for rotating the limb shape about the braider plane in order to accommodate a curved limb shape representing a truncated limb with ankle and foot.

10. The method of claim 7 further comprising a method for extracting the angled limb shape by motion of a second linear gantry to complete the braiding process.

\* \* \* \* \*